United States Patent [19]

Schulze et al.

[11] 4,191,615

[45] Mar. 4, 1980

[54] PROCESS FOR OPERATING EXTRACTION OR EXTRACTIVE DISTILLATION APPARATUS

[75] Inventors: Martin Schulze, Neviges; Gerhard Preusser, Essen, both of Fed. Rep. of Germany

[73] Assignee: Krupp-Koppers GmbH, Essen, Fed. Rep. of Germany

[21] Appl. No.: 863,733

[22] Filed: Dec. 23, 1977

Related U.S. Application Data

[63] Continuation of Ser. No. 641,021, Dec. 15, 1975, abandoned.

[30] Foreign Application Priority Data

Dec. 17, 1974 [DE] Fed. Rep. of Germany ....... 2459534

[51] Int. Cl.$^2$ .......................... B01D 3/40; C23F 11/00
[52] U.S. Cl. ........................................... 203/3; 203/7; 203/33; 203/35; 203/43; 203/51; 203/58; 208/326; 252/387; 422/7; 585/855; 585/860
[58] Field of Search .................... 203/3, 7, 35, 33, 51, 203/58, 43; 260/674 R, 674 SE, 666.5; 208/47, 313, 326; 21/2.5 R, 2.7 R; 252/387

[56] References Cited

U.S. PATENT DOCUMENTS

| | | | |
|---|---|---|---|
| 2,199,180 | 4/1940 | Laughlin | 252/387 |
| 2,416,500 | 2/1947 | Scarth | 203/7 |
| 2,908,640 | 10/1959 | Dougherty | 208/47 |
| 3,030,308 | 4/1962 | Agnew | 252/387 |
| 3,325,399 | 6/1967 | Cinelli et al. | 260/674 SE |
| 3,679,579 | 7/1972 | Preusser et al. | 208/326 |
| 3,723,347 | 3/1973 | Mitchell | 252/387 |
| 3,764,548 | 10/1973 | Redmore | 252/387 |
| 3,808,140 | 4/1974 | Mago | 252/387 |
| 3,923,539 | 12/1975 | Jorns | 252/387 |
| 3,951,844 | 4/1976 | Mago et al. | 252/387 |

*Primary Examiner*—Wilbur L. Bascomb, Jr.
*Attorney, Agent, or Firm*—Michael J. Striker

[57] ABSTRACT

In order to prevent corrosion of the apparatus in extraction and extractive distillation processes where N-substituted morpholine is employed as the selective solvent an additive is added to the solvent which additive consists of (a) phosphoric acid, (b) a salt thereof, (c) a vanadium compound, (d) a molybdenum compound or (e) a mixture of two or more of these compounds, the addition being effected in an amount of about 0.005 to 0.02% by weight of the morpholine solvent.

9 Claims, 1 Drawing Figure

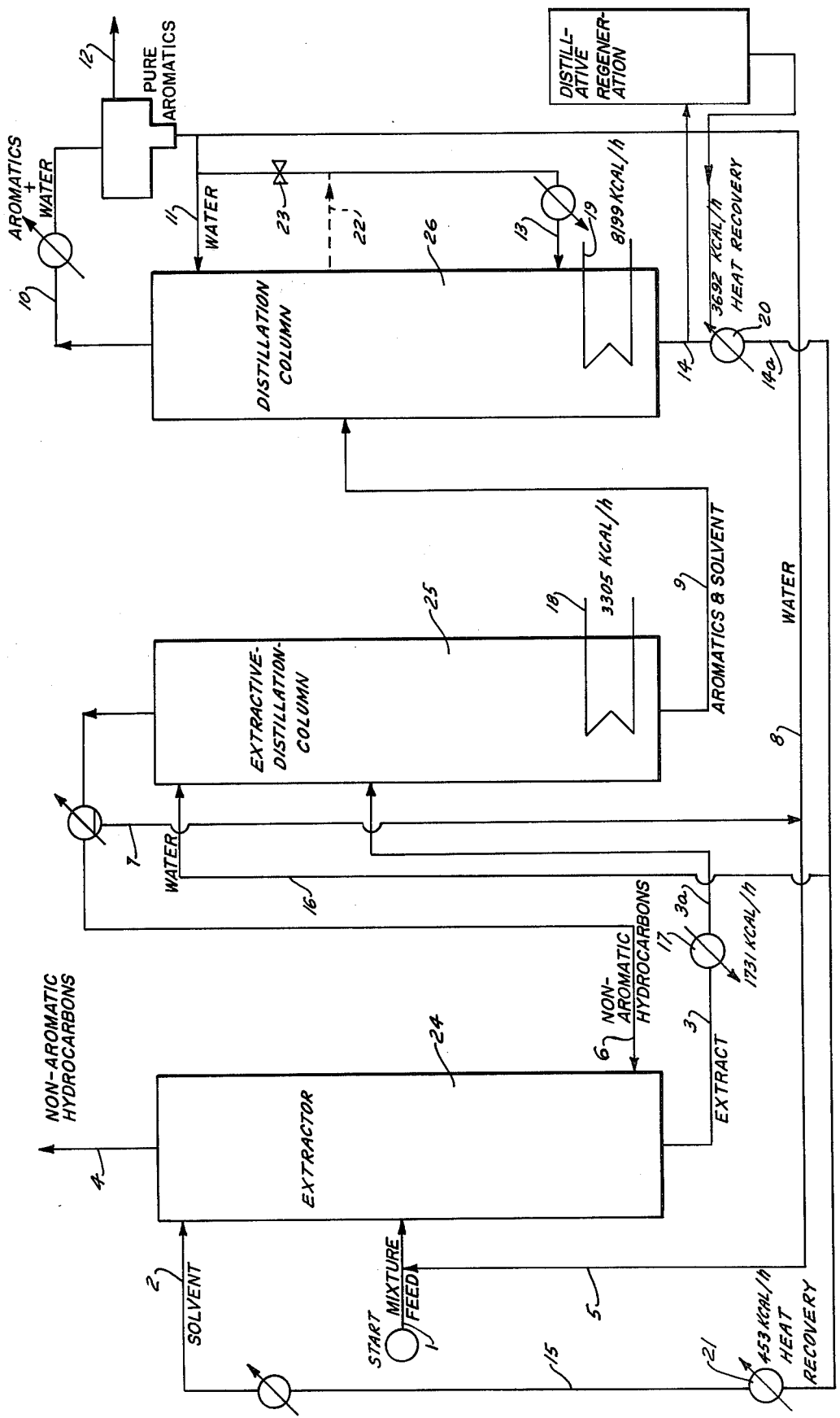

PROCESS FOR OPERATING EXTRACTION OR EXTRACTIVE DISTILLATION APPARATUS

This is a continuation of application Ser. No. 641,021, filed Dec. 15, 1975, now abandoned.

BACKGROUND OF THE INVENTION

The invention relates to a manner of operating extraction apparatus or extractive distillation apparatus or a combination of both apparatus for the purpose of recovery of pure hydrocarbons.

Installations of this type are presently used on a large industrial scale, particularly where it is desired to obtain pure aromatic compounds, for instance from a mixture of aromatic and non-aromatics. In these processes the selective solvent is preferably taken from the group of the N-acyl derivatives of morpholine, specifically N-formylmorpholine. Normally, the extraction is in the manner of a liquid-liquid extraction where the solvent is employed together with water. In the so-called extractive distillation, however, the operation is usually carried out with anhydrous solvent. A prior art process described in German Pat. No. 2,040,025 operates with a combination of liquid-liquid extraction and extractive distillation. Reference regarding this type of combination apparatus is also made to U.S. Pat. No. 3,554,873.

In the apparatus used in these processes there were noticed in a number of cases corrosion phenomena for which at first there was no plausible explanation. The corrosion appeared particularly at those parts of the apparatus which were exposed to strong attacks by vapors and liquids as for instance is the case with the boiler pipes at the bottom of the distillation column or of the extractive distillation column. Among the experts it was generally believed, as for instance expressed in the German published application 1,545,365, column 2, lines 35 to 43, that the corrosion was caused by hydrolysis or disociation products resulting from the morpholine derivatives used as solvents. Careful investigations of the applicants have however not confirmed this assumption.

An attempt was also made to solve the problem by employing methods used in gas washing apparatus for the purpose of preventing corrosion. In these apparatus the amino solutions of tartaric acid were used in combination with compounds of the 4th and 5th group of the periodic system. However, this method also did not have a satisfactory result.

The present invention therefore has the object to provide for means to prevent the corrosion phenomena set out above. Implied in this object is also the problem to find the cause of the corrosion which in the past was entirely unknown.

SUMMARY OF THE INVENTION

The problem of the invention is met by adding to the N-substituted morpholines used as selective solvent an additive consisting of (a) phosphoric acid, (b) a salt thereof, (c) a vanadium compound, (d) a molybdenum compound or (e) a mixture of two or more of these compounds of (a) to (d), the said addition being effected in the amount of about 0.005 to 0.02% by weight of the morpholine solvent.

BRIEF DESCRIPTION OF THE DRAWING

The drawing shows in diagrammatic form an apparatus used in the extraction of benzene, toluene and xylene from reformate gasoline in which N-formylmorpholine is used as the selective solvent together with the special additives of the invention.

DISCUSSION OF THE INVENTION AND OF PREFERRED EMODIMENTS

The present invention is based on a new realization of the causes of the corrosion of the apparatus in the extraction and extractive distillation processes. The inventors have found that the corrosion is principally due to the free acid ions which are entrained into the extraction apparatus by the initial hydrocarbon mixture used as the starting product. These ions involve principally free chlorides and sulfate ions which originate in the pretreatment of the hydrocarbon mixture.

For instance, it was found that when using a so-called reformate, free chloride ions were brought into the extraction apparatus because in the preceding reforming step the catalyst had been activated with propyl chloride. This led to the formation of free hydrochloric acid. Regardless of the subsequent distillation of the reformate there remained an amount of chloride ions in the hydrocarbon product which was too small to be detected by normal analytical methods. These chloride ions then found their way into the extraction apparatus where they were absorbed in the basic solvent and gradually increased in their concentration in the solvent. For instance, in the case where the reformate which constituted the starting product contained an amount of free chloride ions of 0.5 ppm, this amount could not be detected with the analytical methods used in actual industrial practice. However, at an hourly throughput of 40 t of initial product an amount of 15.84 kg of free chloride ions accumulated in the solvent circulating in the extraction apparatus in the course of 33 operating days. If it is assumed that the total circulating amount of solvent in this case was about 200 t the concentration of free chloride ions in the solvent was about 80 mg $Cl^-$ per liter. This amount was definitely sufficient to cause corrosion phenomena during prolonged times in those parts of the apparatus which were in contact with the solvent.

Similar conditions exist for instance with free sulfate ions in those cases where the initial hydrocarbon mixture has been subjected to a sulfuric acid wash (acid raffination) prior to passing into the extraction apparatus.

The N-substituted morpholines which can be used as selective solvents in the processes of the inventions are for instance the following:
  (a) acylmorpholines:
  N-formylmorpholine
  N-acetylmorpholine
  N-propionylmorpholine
  (b) alkylmorpholines:
  N-ethylmorpholine
  N-butylmorpholine
  N-methylmorpholine
  N-($\beta$-hydroxyethyl)-morpholine These selective solvents are particularly useful where pure aromatics are to be recovered in a large scale industrial process from a mixture of the aromatics with nonaromatics. These processes are for instance used in relation to the following products:
  (a) reformates which are made in reforming processes for improving the octane number of automotive fuels. A typical composition of such reformate will be set out below in a specific example.

(b) pyrolysis gasoline which is obtained in a cracking process for making ethylene and propylene. The pyrolysis gasoline in these cases is obtained as a by-product. Depending on the operation of the cracking process it may contain up to 85% by weight of aromatics such as benzene, toluene, xylene and ethylene benzene.

(c) crude benzene as it is obtained in making coke from coal. From this crude benzene pure benzene can be obtained in several process steps as a raw material for the chemical industry. Usually, in these process steps an extractive distillation is included to remove the non-aromatics from the benzene.

The amount of solvent used in all of these processes normally is between 1.5 and 7 times, particularly between 2 and 5 times the amount of the starting product expressed by weight.

The additives employed according to the present invention are particularly phosphoric acid and ammonium-, sodium-, potassium- and aminophosphates. Furthermore, alkali- and ammonium vanadates and alkali- and ammonium molybdates.

The preferred compounds of the inventions for use as additives are orthophosphoric acid ($H_3PO_4$), vanadium pentoxide ($V_2O_5$), and molybdenum ($MoO_3$). While the general range of addition is between 0.005 and 0.02% by weight of the morpholine solvent, the preferred range is between 0.006 and 0.01% by weight.

It has also been found that preferably the contents in the solvent of free acid ions is continuously checked during the process of recirculating the solvent. As soon as the contents of free acid ions in the solvent is found to reach an amount between 0.005 and 0.01% by weight part of the circulating solvent is split off and subjected to a distillative regeneration. This regeneration of the circulating solvent is continued until the contents of free acid ions has been reduced to between 0.0005 and 0.001% by weight.

In the following comparative examples a so-called reformate was subjected to a combined liquid-liquid extraction and extractive distillation. The contents of free chloride ions in this product could not be detected by normal analytical processes used in industrial practice.

Generally, the operation involved subjecting a hydrocarbon mixture which contained an aromatic and a non-aromatic component to a liquid-liquid extraction with a solvent consisting of N-formylmorpholine and water of a concentration that the solubility for the aromatic component was appreciable, while the solubility for the non-aromatic component was less than that for the aromatic component. In this step there was then formed an extract which included a substantial portion of the aromatic component and a portion of the non-aromatic component. The extract was then passed into an extractive distillation zone in which a solvent was used consisting also of formylmorpholine and water. The solvent was caused to flow in counter-current to the vapors from the extract. There was formed in the extractive distillation a solvent which differed from the first solvent only in the lower water concentration. The water concentration of the second solvent was such that its solubility for the aromatic component was appreciable while the solubility for the non-aromatic component exceeded that of the solvent used in the liquid-liquid extraction. The aromatic components were then separated by distillation from the second solvent.

More specifically reference is now made to the attached drawing.

The charge 1 was introduced into the 28th tray of the perforated tray extractor 24 which was provided with 60 trays. To the charge water was added via ducts 8 and 5 from the head of the distillation column 26 in an amount that the water contents in the bottom portion of the extractor was 5 percent by weight of the solvent.

The separated solvent was then charged via duct 2 into the head portion of the extractor 24. Via duct 4 the non-aromatics were discharged from the extractor 24. The extract passed via duct 3 and heat exchanger 17 into the 30 th tray of the extractive distillation column 25 which was provided with 50 trays. Additional separate solvent at a temperature of 70° C. was charged through duct 16 into the head portion of the column 25. The water separated from the head product of col. 25 was condensed and the water phase was passed to the extractor 24 via ducts 7 and 5. The non-aromatic hydrocarbon phase was passed via duct 6 as a counter-solvent into the bottom portion of the extractor 24. The column 24 was operated without reflux.

The bottom product of column 25 was passed via duct 9 to a distillation column 26 provided with 25 trays. The pure aromatics and the major portion of the water were withdrawn at the head via a duct 10. The water reflux via duct 11 was adjusted to 0.25 kg water/kg pure aromatics as was also done in the experiments related to the U.S. patent. The remaining water was recycled through ducts 8 and 5.

Water that had evaporated in the heat exchanger 20 was passed via duct 13 as stripper steam into the bottom portion of the distillation column. The bottom temperature was 166° C.

The pure aromatics were discharged from the system through duct 12.

The components and solvents used in the initial feed in this process were as follows (% by weight):

|  |  | Solvent |
| --- | --- | --- |
| benzene | 14.8 | 0.004 |
| toluene | 24.3 | 0.049 |
| $C_8$ aromatics | 24.8 | 0.420 |
| non-aromatics | 36.1 | — |

The apparatus and process of operating it is further described in Application Serial No. 526,367 filed Nov. 22, 1974 by the present inventors together with two coinventors.

EXAMPLE A

In this Example the just-described process was carried through with the apparatus also described and a solvent consisting only of N-formylmorpholine and water. No further attention was given to the contents of acid ions in the solvent. With this type of operation after 3 months there was already apparent distinct corrosion in those parts of the apparatus which were in contact with the solvent. This was particularly pronounced in case of the boilers in the bottom of the distillation columns.

EXAMPLE B

The same operation with the same process in the same solvent was carried out as in Example A and as described before. However, in this case phosphoric acid ($H_3PO_4$) was added in an amount of 0.007% by weight of the morpholine. Furthermore, the contents of chloride ions in the circulating solvent was continuously controlled. As soon as the contents had reached an amount of 0.0075% by weight, part of the circulating solvent as received from the distillation column 26 was split off from duct 8 prior to passing it back into the extraction column 24 and was subjected to a distillative regeneration. This regeneration was continued until the chloride ion concentration in the circulating solvent had been reduced to an amount of 0.00075% by weight.

All other conditions of operation and apparatus used were exactly the same in this example as in Example A. After 3 months, however, there could not be found any corrosion of the apparatus in the operation where the additive had been used with the morpholine solvent. Even after a 6 months operation corrosion did not yet show up. This shows the superiority of the process of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. The improvement in a process for recovery of pure hydrocarbon compounds from a hydrocarbon mixture containing free acid ion impurities by a solvent extractive process and subsequent isolation of said pure hydrocarbon compounds from a solvent system in which process an N-substituted morpholine is employed as the selective solvent, said improvement comprising adding to said morpholine solvent or a mixture thereof with a minor amount of water at least one of the following compounds: phosphoric acid, a salt thereof, an inorganic vanadium compound or an inorganic molybdenum compound, said addition being effected in an amount of about 0.005 to 0.02% by weight of the morpholine solvent, continuously recycling the solvent mixture containing said additive recovered from said isolation process back to said solvent extractive process and continuously determining the contents of free acid ions absorbed by said solvent from said hydrocarbon mixture and, as soon as the contents of acid ions reaches an amount of about 0.005 to 0.01% by weight of the solvent mixture, removing at least a portion of the circulating solvent and subjecting it to regenerative distillation to separate the free acid ion containing components, thus effecting the regeneration of the solvent, and continuing the distillation until the content of free acid ions is reduced to an amount between about 0.0005 and 0.001% by weight, whereby the acid ions entrained in said hydrocarbon mixture from preceding treatments applied to said mixture are substantially reduced and corrosion caused thereby is prevented.

2. The improvement of claim 1 wherein the addition is made in an amount of about 0.006 to 0.01% by weight of the morpholine solvent.

3. The improvement of claim 1 wherein the additive is at least one compound selected from the group consisting of phosphoric acid ($H_3PO_4$), vanadium pentoxide ($V_2O_5$) and molybdenum trioxide ($MoO_3$).

4. The improvement of claim 1 wherein the additive is selected from the group consisting of ammonium phosphate, sodium phosphate, potassium phosphate, an amino phosphate and combinations of two or more of these compounds.

5. The improvement of claim 1 wherein the additive is selected from the group consisting of an alkali vanadate, an ammonium vanadate, an alkali molybdate, an ammonium molybdate and combinations of two or more of these compounds.

6. The process of claim 1 wherein the said acid ions are chloride or sulfate ions.

7. The improvement of claim 1, wherein said solvent extractive process comprises extractive distillation.

8. The improvement of claim 1, wherein said solvent extractive process comprises liquid-liquid extraction.

9. The improvement of claim 1, wherein said solvent extractive process comprises a combination of liquid-liquid extraction and extractive distillation.

* * * * *